United States Patent
Sandison et al.

[11] Patent Number: 5,446,197
[45] Date of Patent: Aug. 29, 1995

[54] METHOD OF PURIFYING ACIFLUORFEN

[75] Inventors: Mark Sandison, Dearborn, Mich.; Ron Eva, Bahama, N.C.; Lawrence E. James, Grosse Ile, Mich.

[73] Assignee: BASF Corporation, Mount Olive, N.J.

[21] Appl. No.: 78,993

[22] Filed: Jun. 17, 1993

[51] Int. Cl.⁶ ............................................. C07C 205/00
[52] U.S. Cl. ................................................... 562/435
[58] Field of Search ......................................... 562/435

[56] References Cited

U.S. PATENT DOCUMENTS

| Re. 31,455 | 12/1983 | Bayer et al. | 71/115 |
| 4,350,522 | 9/1982 | Bayer et al. | 71/111 |
| 4,594,440 | 6/1986 | Giacobbe et al. | 560/21 |

FOREIGN PATENT DOCUMENTS

| 0022610 | 1/1981 | European Pat. Off. | 562/435 |
| 2501797 | 10/1975 | Germany | 562/435 |
| 3319287 | 11/1984 | Germany | 562/435 |
| 2103214 | 2/1983 | United Kingdom . | |

Primary Examiner—Marianne M. Cintins
Assistant Examiner—Keith MacMillan
Attorney, Agent, or Firm—Nixon & Vanderhye

[57] ABSTRACT

A method of purifying acifluorfen to achieve a purity of greater than about 85% by weight involves heating to dissolution a solution of an acifluorfen crude wet cake and at least one solvent from the group of 1,2-dichlorobenzene, monochlorobenzene, o-xylene and p-xylene, with the solution having from about 10 to about 30 weight percent of acifluorfen crude wet cake. The solution is then cooled until crystals of purified acifluorfen form. The crystals are then filtered at a temperature within the range of from about 0° to about 30° C. The filtered crystals are then recovered.

6 Claims, No Drawings

METHOD OF PURIFYING ACIFLUORFEN

FIELD OF THE INVENTION

The present invention relates to a method of purifying acifluorfen to achieve greater purity and yield. The invention also relates to the product so produced.

BACKGROUND OF THE INVENTION

Acifluorfen is a well known herbicide used widely in a variety of agricultural applications. Its chemical name is 5-(2-chloro-4-(trifluoromethyl)phenoxy)-2-nitrobenzoic acid and it is currently available from BASF Corporation under the trademark BLAZER®. U.S. Pat. Nos. 4,350,522, Re. No. 31,455 and Re. No. 31,731 all relate to the production of acifluorfen and its related salts. The synthetic route used to produce acifluorfen is illustrated below. The initial step in the synthesis is the reaction between 3-hydroxybenzoic acid (mHBA) and 3,4-dichlorobenzyltrifluoride (3,4-DCBTF) in the presence of potassium hydroxide (KOH) and dimethyl sulfoxide (DMSO) to form 3-(2-chloro-4-(trifluoromethyl)phenoxy)benzoic acid with a small amount of 3-(2-chloro-5-(trifluoromethyl)phenoxy)benzoic acid. The product is then nitrated in a mixture of $HNO_3/H_2SO_4$/acetic acid/acetic anhydride, precipitated by the addition of water, and filtered to provide crude acifluorfen:

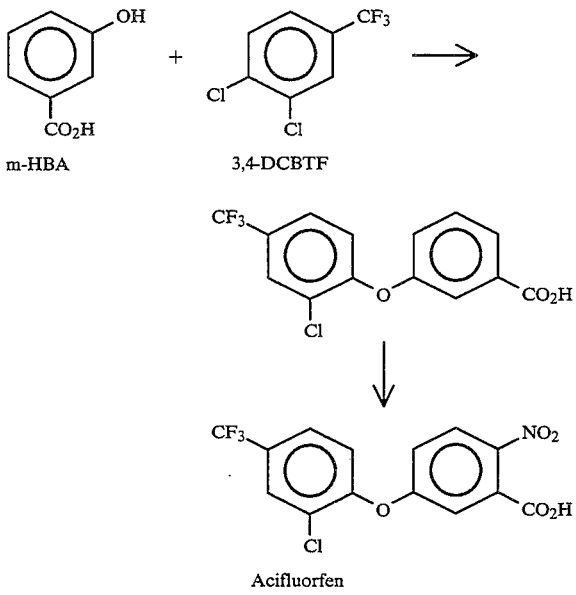

Unfortunately, synthetically produced acifluorfen very often contains a fairly high percentage of isomeric impurities. It is conceivable that acifluorfen may be utilized as an intermediary in the synthesis of other compounds, and therefore it is chemically important to have a very pure acifluorfen starting product so as to produce high final yields of other chemical products.

Three compounds in particular should be removed from the manufactured acifluorfen product. The nitration of 3-(2-chloro-4-(trifluoromethyl)phenoxy)benzoic acid (unnitrated intermediate) produces, in addition to acifluorfen, 3-(2-chloro-4-(trifluoromethyl)phenoxy)-2-nitrobenzoic acid (hereinafter 2'-NO₂ isomer). Also produced in this synthesis is 3-(2-chloro-4-(trifluoromethyl)phenoxy)-4-nitrobenzoic acid (hereinafter 6'-NO₂ isomer). The nitration of the 3-(2-chloro-5-trifluoromethyl) phenoxy)benzoic acid, present as a by-product in the synthesis route, produces 5-(2-chloro-5-(trifluoromethyl)phenoxy)-2-nitrobenzoic acid (hereinafter 5-CF₃ isomer):

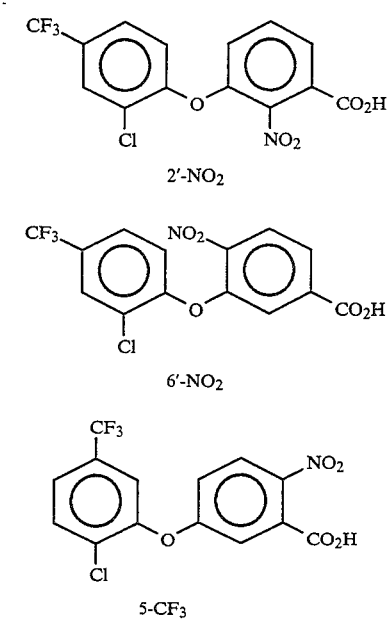

Typically, the crude acifluorfen contains about 80–85% of acifluorfen, 9–10% of the 2'-NO₂ isomer, 3–4% of the 6'-NO₂ isomer, and 4–5% of the 5-CF₃ isomer and less than 1% unnitrated intermediate on a dry basis. These percentages may of course vary depending upon the particular reaction components and parameters utilized by those skilled in the art. In any event, there remains the problem of a substantial number of the aforementioned impurities present in the manufactured acifluorfen.

Many chemical purification processes involve dissolution of the preferred compound together with its impurities in a solvent, and then recrystallization of the desired compound. Typically, the final yield of the desired compound is smaller via the purification route. For this reason, care must be taken so as not to sacrifice yield for purity.

There presently exists a need in the art to purify acifluorfen so as to remove undesirable isomers. At the same time, there is also a need to maintain substantially high final yields of the purified acifluorfen product.

OBJECTS OF THE INVENTION

It is therefore an object of the present invention to provide a process for the purification of acifluorfen.

A further object of the invention is to obtain a high yield of purified acifluorfen.

Another object is to provide purified acifluorfen which is suitable for use in a wide variety of agricultural and chemical applications.

A further object is to obtain highly purified acifluorfen which can in turn be utilized in the chemical syntheses of other end-use products.

Another object is to provide acifluorfen which meets Environmental Protection Agency (EPA) standards for registration.

SUMMARY OF THE INVENTION

These and other objects of the invention are achieved by providing a method of purifying acifluorfen to achieve a purity of greater than about 85% by weight. This process involves heating to dissolution a mixture of an acifluorfen crude wet cake and at least one of the solvents 1,2-dichlorobonzene, monochlorobenzene, orthoxylene and para-xylene with or without water. The solution will have about 10 to about 30 weight percent of acifluorfen crude wet cake. The remainder of the solution will be one or more of the aforementioned solvents. After dissolution, the mixture of acifluorfen crude wet cake is cooled until crystals of purified acifluorfen form. These crystals are then filtered at a temperature within the range of from about 0° to about 30° C. Once filtered, the purified acifluorfen crystals are then recovered.

As that term is used herein, "acifluorfen crude wet cake" refers to a mass of unpurified, synthetically manufactured acifluorfen having roughly about 60 parts of acifluorfen, about 20 parts total of the isomers 2'-NO$_2$, 6'-NO$_2$, and 5-CF$_3$, and about 20 parts of water. On a dry basis this translates into about 80–85% of acifluorfen, 9–10% of the 2'-NO$_2$ isomer, 3–4% of the 6'-NO$_2$ isomer, and 4–5% of the 5-CF$_3$ isomer. Those skilled in the art will recognize that other wet cakes of unpurified acifluorfen may be formulated wherein the relative weight percentages of acifluorfen, isomers, and water will vary from the aforestated ranges. It is also within the scope of the invention that the unpurified acifluorfen need not be in the form of a solid wet cake prior to purification. Thus, it is contemplated that the purification process of the invention will be adaptable to most any unpurified acifluorfen containing more than de minimis amounts of undesirable isomers.

Also provided as part of the invention is a method of purifying acifluorfen to achieve a purity of at least about 90%, as well as yield greater than or equal to 80% by weight, which also involves heating to dissolution a solution of an acifluorfen crude wet cake and at least one of the solvents 1,2-dichlorobenzene, monochlorobenzene, ortho-xylene and para-xylene. The solution will have about 10 to about 30 weight percent of acifluorfen crude wet cake. The remainder of the solution will be one or more of the aforementioned solvents. After dissolution, the solution of acifluorfen crude wet cake is cooled, the resulting crystals of purified acifluorfen are then filtered at a temperature within the range of from about 0° to about 30° C., and the crystals are recovered.

In another embodiment of the invention, acifluorfen is purified using 1,2-dichlorobenzene as the solvent to achieve a purity of at least about 92% and a yield of at least about 80%. The final dry weight ratio of acifluorfen to the 2'-NO$_2$ isomer is 25 also at least about 23:1. This method utilizes 1,2-dichlorobenzene solvent in which a crude acifluorfen wet cake is dissolved. The crude wet cake comprises from about 10 to about 25 weight percent of the solution. The solution is heated to dissolution and then cooled. The purified crystals of acifluorfen which then form are filtered at a temperature of from about 10° to about 20° C., and collected.

The invention also provides acifluorfen which has been purified according to one or more of the process embodiments set forth herein.

DETAILED DESCRIPTION OF THE PREFERRED EMBODIMENTS

Unless otherwise specified, all quantities set forth as percentages herein are expressed in terms of weight.

Acifluorfen may be purified to greater than about 85% on a dry weight basis, more preferably greater than about 87%, and even more preferably greater than about 90%, 92%, 94%, 96%, or even 98% by utilizing the procedures set forth herein. In certain embodiments, the process of the invention will also result in acifluorfen final yields of greater than about 80 or 82% by weight, more preferably in excess of about 84% or greater by weight. It is especially desirable to have both high final yield and purity of acifluorfen. Preferably, the ratio of purified acifluorfen to the 2'-NO$_2$ isomer will be in excess of about 23 to 1. At the same time, it is also especially desirable to have deminimis amounts of the other undesirable isomers.

In order to purify acifluorfen, a crude wet cake is first prepared or obtained. The crude wet cake may be prepared in accordance with the procedure heretofore set forth for the known production of acifluorfen. Briefly, after the crude product is nitrated in the acetic acid mixture, water is then added, which causes the product to precipitate. This product is in turn filtered and the resulting mass is what is referred to as the crude wet cake.

While the weight of the crude wet cake may vary according to user requirements, a typical acifluorfen wet cake to be purified on a laboratory scale may weigh anywhere from about 25 grams to 1,000 grams, preferably from about 100 grams to about 500 grams, more preferably from about 100 grams to about 300 grams.

While percentages of the individual constituents may vary, it is typically expected that the weight percentages for acifluorfen in the crude wet cake will be in the range of about 55 to about 65%, preferably from about 60 to about 65%, and more preferably from about 62 to about 65%. (It is desirable to have as much acifluorfen in the crude wet cake as possible.) The 2'-NO$_2$ isomer will be present in ranges from about 5 to about 7%, preferably from about 5 to about 6%, and more preferably, from about 5 to about 5.5%. The 6'-NO$_2$ isomer typically ranges from about 3 to about 5% of the total crude wet cake composition, preferably, from about 3 to about 4%, and more preferably from about 3 to about 3.5%. The weight percentages of the 5-CF$_3$ isomer range as follows: about 2 to about 3.5%, preferably from about 2 to about 3%, and more preferably from about 2 to about 2.5%. In all instances, water will make up the remainder of the crude wet cake. Typically, water comprises about 15 to about 25% of the crude wet cake.

The crude wet cake is then dissolved in solution with at least one solvent from the group of 1,2-dichlorobenzene, monochlorobenzene, ortho-xylene and para-xylene. Of these, monochlorobenzene and 1,2-dichlorobenzene are preferred. 1,2-dichlorobenzene is particularly preferred.

The crude wet cake will comprise from about 10 to about 30 weight percent of the solution. As an example, a 30% crude wet cake solution would contain 30 grams of crude wet cake and 70 grams of solvent. In a preferred mode, the solution will contain from about 15 to about 25 weight percent of crude wet cake, more preferably from about 15 to about 21 weight percent. In some embodiments when 1,2-dichlorobenzene is the solvent, about 10 to about 20 weight percent, and more preferably from about 15 to about 21 weight percent of crude wet cake may be utilized in solution.

To dissolve the crude wet cake and solvent on a laboratory scale, it is preferred to utilize an Erlenmeyer flask equipped with a magnetic stirrer. The flask may be fitted with a Claisen adapter, a Dean-Stark trap, a cold water condenser, as well as other laboratory apparatus.

The solution is then heated until dissolution occurs, and then held at that temperature for a period of time, preferably from about 10 to about 50 minutes, more preferably about 20 to about 40 minutes, and even more preferably about 30 minutes. The skilled artisan may find that heating time may vary from the above. During the period of dissolution, the water from the crude wet cake is preferably removed, and a Dean-Stark trap is especially desirable to accomplish this. It is also within the scope of the invention that the water not be removed during the period of dissolution.

The solution is then cooled at a rate within the range of about 20° to about 25° C. per hour. Those skilled in the art will recognize that the above rate of cooling should facilitate crystallization, but the rate of cooling does not appear to be critical and may be varied as desired. When the temperature of the solution reaches approximately 60° C., those skilled in the art may initiate the optional step of "seeding" the solution with "pure" acifluorfen crystals. These crystals may be obtained from sources known in the art, for example from a double recrystallization of crude wet cake from toluene. Upon seeding, crystals of pure acifluorfen begin to form.

Upon cooling to the desired temperature as further set forth herein, crystallization of purified acifluorfen continues. For the filtration step, the solution should be cooled to a temperature within the range of about 0° to about 30° C. Preferably, the filtration temperature should be within the range of about 10° to about 30° C., more preferably from about 15° to about 30° C. When 1,2-dichlorobenzene is utilized as the solvent, those skilled in the art may find that a temperature range of from about 10° to about 20° C. may give excellent results in terms of both final purity and yield. Filtration may be effected with laboratory and industrial instruments known in the art.

Once formed, the resulting crystals are preferably filtered at temperatures within the ranges just set forth. If desired, the crystals may also be washed with cold (~5° C.) fresh solvent.

The filtered crystals may then be analyzed to determine both the remaining quantities of impurities and the final yield of acifluorfen by high pressure liquid chromatography. The external standard method is typically used for quantitation. As an example, a working standard was obtained which had the following composition by dry weight percent of the acid form: 81.3% for the acifluorfen, 8.21% for the 2'-$NO_2$ isomer, 3.66% for the 6'-$NO_2$ isomer, and 4.38% for the 5-$CF_3$ isomer. The detection limit for the various compounds was approximately 0.1%.

The following examples are further provided by way of illustration, and should in no way be construed as limiting the scope of the invention.

EXAMPLE 1

Example 1 is provided by way of comparison to show that not all solvents can be utilized in the process according to the various embodiments of the invention.

For this experiment, a 200 gram crude acifluorfen wet cake was obtained from BASF Corp. This material had the following composition (in weight percent of the acid):

|  | Production Site Certificate of Analysis | BASF Corp. Research Services Analysis |
|---|---|---|
| $H_2O$ | 21.4 | not tested |
| 5-$CF_3$ | 2.5 | 2.8 |
| Acifluorfen | 61.3 | 61.4 |
| 2'-$NO_2$ | 6.2 | 6.5 |
| 6'-$NO_2$ | 3.7 | 3.5 |

For each experiment, a 500 mL Erlenmeyer flask fitted with a Claisen adapter, a Dean-Stark trap, and a cold water condenser was used. Filtrations were accomplished with a Buchner funnel and Whatman 50 filter paper.

A 15% solution of acifluorfen crude wet cake and solvent was heated to reflux with magnetic stirring and held at reflux for 30 minutes. The water from the crude wet cake was removed via the Dean-Stark trap. The solution was then cooled at a rate of 20°–25° C./hour until the temperature reached 60° C. At that point, the solution was seeded with "pure" acifluorfen crystals. The "pure" acifluorfen was obtained by a double recrystallization of the crude wet cake from toluene. After further cooling to 30° C. (at the above rate) the mixture was filtered. The solids were washed with 10 mL of fresh solvent at ambient temperature and analyzed by HPLC. The results for each particular solvent utilized are set forth in TABLE 1 below:

TABLE 1

| Solvent | 15% Crude Wet Cake Weight Percent | | | | Acifluorfen Yield | Aci./2'-NO2 Ratio |
|---|---|---|---|---|---|---|
|  | 5-CF3 | Acifluorfen | 2'-NO2 | 6'-NO2 | | |
| m-Xylene | 0.8 | 83.4 | 5.5 | ND | 79% | 15.2 |
| DI Water | 2.8 | 73.4 | 8.0 | 4.7 | 98% | 9.2 |
| o-Xylene |  | 87.5 | ND | ND | 64% | *** |
| Heptane |  | 72.0 | 8.9 | 4.8 | 91% | 8.1 |
| Benzene |  | 79.9 | 8.2 | ND | 63% | 9.7 |
| Xylene | ND | 84.1 | 6.0 | ND | 74% | 14.0 |
| Ethylene dichloride | ND | 85.5 | 3.5 | ND | 59% | 24.4 |
| Toluene | 0.9 | 81.2 | 6.4 | ND | 72% | 12.7 |
| 1,2-dichlorobenzene | 1.3 | 83.6 | ND | ND | 80% | *** |
| p-Xylene | 1.0 | 84.9 | ND | ND | 75% | *** |
| Chlorobenzene | 1.0 | 92.6 | ND | ND | 74% | *** |

ND = None detected
*** = No. 2'-NO2 isomer detected

The Example 1 experiments were designed to obtain initial screening results as quickly as possible by testing 18 different solvents. Seven of the solvents not appearing in TABLE 1 (N-methyl pyrrolidone, acetonitrile, ethylene glycol dimethylether, ethylene glycol diethyl ether, methyl ethyl ketone, methyl amyl ketone, and 2-methoxy ethylether) were immediately dismissed as suitable solvents because the acifluorfen crude wet cake was completely soluble therein at ambient temperature, even at a 30% level at ambient temperature, and would therefore result in an unacceptably low acifluorfen recovery from the recrystallization.

As can also be seen from the results, all the solvents with the exception of o-xylene, p-xylene, monochlorobenzene, and 1,2-dichlorobenzene resulted in unacceptably low purity or yield levels, or had a small or very small acifluorfen to 2'-NO$_2$ isomer ratio (well below the especially desirable ratio of about 23:1).

EXAMPLE 2

The Example 2 experiments were designed so that solutions of 15, 22.5, and 30% acifluorfen crude wet cake were filtered at 0°, 15°, and 30° C. for each of the four selected solvents o-xylene, p-xylene, monochlorobenzene and 1,2-dichlorobenzene- The Example 2 experimental procedure was the same as in Example 1 with the exceptions that the filtered solids were washed with 10 mL of cold fresh solvent, and the solids were dried under vacuum at 60° C. prior to analysis. The results are set forth in TABLE 2:

as the solvent. It is desirable to have a final purified acifluorfen to 2'-NO$_2$ ratio of at least about 23 to 1. Embodiments wherein no 2'-NO$_2$ levels are detected by analysis are especially desirable. In certain embodiments, a dry weight percentage for each of the 6'-NO$_2$ and 5-CF$_3$ isomers can be less than or equal to about 2%, preferably less than or equal to about 1%. Concentrations less than the analytical detection limits for each of these isomers may also be attained.

TABLE 3 below shows these results for solutions with varying crude wet cake percentages, as well as filtration temperatures. The Experimental regimen set forth in Example 2 yielded the results in TABLE 3:

TABLE 3

ACIFLUORFEN RECRYSTALLIZATION FROM ODCB

| % Crude Wet Cake | Filtration Temp. | Normalized | | | Percent Yield |
|---|---|---|---|---|---|
| | | Acifluorfen | 5-CF$_3$ | 2'-NO2 | |
| 15 | 10 | 99.0% | 1.0% | ND | 84.3% |
| | 15 | 99.0% | 1.0% | ND | 81.7% |
| | 20 | 99.2% | 0.8% | ND | 82.1% |
| 18 | 10 | 94.5% | 0.7% | 4.8% | 85.8% |
| | 15 | 95.3% | ND | 4.7% | 85.7% |
| | 20 | 94.9% | 0.7% | 4.4% | 83.8% |
| 21 | 10 | 94.3% | ND | 5.7% | 89.3% |
| | 15 | 94.6% | ND | 5.4% | 87.3% |
| | 20 | 95.4% | ND | 4.6% | 86.6% |

Statistically significant if yield differences are >0.5%.

The acifluorfen purified according to the various embodiments of the invention should find ready application in a variety of agricultural uses. Acifluorfen may be utilized as an herbicide by crop growers according to methods already known in the art. It is also contem-

TABLE 2

| Solvent | Initial % Solids | Filtration Temperature | Analytical | | | | Acifluorfen Yield | Aci/2'-NO2 |
|---|---|---|---|---|---|---|---|---|
| | | | 5-CF3 | Acifluorfen | 2'-NO2 | 6'-NO2 | | |
| o-Xylene | 22.5 | 30 | 0.6 | 91.9 | 8.7 | ND | 85% | 11 |
| | 15.0 | 15 | 0.7 | 90.7 | 5.6 | ND | 85% | 16 |
| | 22.5 | 15 | 0.8 | 92.6 | 8.0 | ND | 89% | 12 |
| | 30.0 | 30 | 0.8 | 91.7 | 7.0 | ND | 89% | 13 |
| | 22.5 | 0 | ND | 89.7 | 6.5 | ND | 93% | 14 |
| | 15.0 | 30 | ND | 97.5 | 2.6 | ND | 72% | 36 |
| | 30.0 | 15 | ND | 92.0 | 7.5 | ND | 91% | 12 |
| | 30.0 | 0 | ND | 91.3 | 7.4 | ND | 94% | 12 |
| | 15.0 | 0 | ND | 91.3 | 7.4 | ND | 86% | 12 |
| p-Xylene | 22.5 | 30 | 0.8 | 92.9 | 7.8 | ND | 89% | 12 |
| | 15.0 | 15 | ND | 92.8 | 5.7 | ND | 84% | 16 |
| | 22.5 | 15 | 0.9 | 92.7 | 7.6 | ND | 92% | 12 |
| | 30.0 | 30 | ND | 90.7 | 8.2 | ND | 88% | 11 |
| | 22.5 | 0 | ND | 86.5 | 8.6 | ND | 92% | 10 |
| | 15.0 | 30 | ND | 92.7 | 5.8 | ND | 77% | 16 |
| | 30.0 | 15 | ND | 90.5 | 6.8 | ND | 93% | 13 |
| | 30.0 | 0 | ND | 91.7 | 7.7 | ND | 93% | 12 |
| | 15.0 | 0 | ND | 91.0 | 6.7 | ND | 86% | 14 |
| MCB | 22.5 | 30 | 1.1 | 95.9 | 3.7 | ND | 65% | 26 |
| | 15.0 | 15 | 1.0 | 92.9 | 3.6 | ND | 83% | 26 |
| | 22.5 | 15 | ND | 92.8 | 5.6 | ND | 90% | 17 |
| | 30.0 | 30 | 1.2 | 92.1 | 7.0 | ND | 89% | 13 |
| | 22.5 | 0 | ND | 89.2 | 6.1 | ND | 91% | 15 |
| | 15.0 | 30 | ND | 96.4 | ND | ND | 70% | *** |
| | 30.0 | 15 | ND | 91.8 | 5.9 | ND | 90% | 16 |
| | 30.0 | 0 | ND | 91.8 | 7.5 | ND | 93% | 12 |
| | 15.0 | 0 | ND | 93.0 | 8.3 | ND | 84% | 11 |
| o-DCB | 22.5 | 30 | 0.8 | 93.5 | 3.0 | ND | 87% | 31 |
| | 15.0 | 15 | 2.3 | 97.4 | ND | ND | 89% | *** |
| | 22.5 | 15 | 1.0 | 92.8 | 6.5 | ND | 95% | 14 |
| | 30.0 | 30 | 1.0 | 90.5 | 9.6 | 0.5 | 88% | 9 |
| | 22.5 | 0 | ND | 90.9 | 7.8 | ND | 92% | 12 |
| | 15.0 | 30 | ND | 99.7 | ND | ND | 79% | ** |
| | 30.0 | 15 | ND | 88.2 | 5.8 | ND | 95% | 15 |
| | 30.0 | 0 | ND | 92.4 | 7.4 | ND | 95% | 12 |
| | 15.0 | 0 | 0.7 | 93.5 | 4.2 | ND | 87% | 22 |

In an especially preferred embodiment of the invention, it is possible to obtain acifluorfen purity well in excess of 95%, and yields greater than about 80% and as high as about 89% when utilizing 1,2-dichlorobenzene plated that the purified acifluorfen product might be utilized in other chemical processes as well, for example as a potential intermediary in the production of other chemical products.

It should also be noted that the method according to the various embodiments of the invention will find ready adaptation in purifying crude acifluorfen which has an initial purity of less than or greater than 80–85%.

While the invention has been described in each of its various embodiments, it is expected that certain modifications thereto may occur to those skilled in the art without departing from the invention's true spirit and scope as outlined in the specification and set forth in the accompanying claims.

What is claimed is:

1. A method of purifying acifluorfen using 1,2-dichlorobenzene solvent to achieve a recrystallized acifluorfen product having an acifluorfen purity of at least about 92%, an acifluorfen yield of greater than about 80%, and a ratio of acifluorfen to 2'-$NO_2$ isomer of at least about 23:1, said method comprising the steps of:
   (a) providing an acifluorfen crude wet cake containing between about 80 to about 85% of acifluorfen crystals on a dry basis;
   (b) heating to dissolution a solution comprised of about 15 weight percent of said acifluorfen crude wet cake and 1,2-dichlorobenzene solvent;
   (c) cooling said solution until recrystallization of said acifluorfen occurs;
   (d) filtering said recrystallized acifluorfen at a temperature within the range of from about 10° to about 20° C.; and
   (e) recovering a product containing said recrystallized acifluorfen having an acifluorfen purity of at least about 92%, an acifluorfen yield of greater than about 80%, and a ratio of acifluorfen to 2'-$NO_2$ isomer of at least 23:1.

2. The method according to claim 1, wherein said purity is at least about 94%, said yield is greater than about 82%, said solution comprises about 15 to about 21% acifluorfen crude wet cake, and said filtration temperature is from about 10° to about 20° C.

3. The method according to claim 2, wherein said purity is at least about 98%, said yield is greater than about 84%, said solution comprises from about 15 to about 21% acifluorfen crude wet cake, and said filtration temperature is from about 10° to about 20° C.

4. The method according to claim 3, wherein said purity is at least about 99%, said yield is greater than about 84%, said solution comprises about 15% acifluorfen crude wet cake, and said filtration temperature is about 10° C.

5. The method according to claim 4, wherein said acifluorfen to 2'-$NO_2$ ratio is at least about 25:1.

6. A method of purifying and recovering acifluorfen comprising the sequential steps of:
   (a) providing an acifluorfen crude wet cake containing between about 80 to about 85% by weight of acifluorfen crystals on a dry basis;
   (b) heating to dissolution a solution consisting essentially of (i) about 15% by weight of said acifluorfen crude wet cake and (ii) at least one solvent selected from the group consisting of monochlorobenzene and 1,2-dichlorobenzene;
   (c) recrystallizing said acifluorfen by cooling said solution to an acifluorfen filtration temperature of from about 10° C. to about 20° C.;
   (d) filtering said recrystallized acifluorfen at said acifluorfen recovery temperature, and then
   (e) recovering said filtered recrystallized acifluorfen to obtain a an acifluorfen product having a purity of at least about 92%, a yield greater than about 80%, and a ratio of acifluorfen to 2'-$NO_2$' isomer of at least about 23:1.

* * * * *